United States Patent
Boehling et al.

(10) Patent No.: US 9,464,029 B2
(45) Date of Patent: Oct. 11, 2016

(54) METHOD FOR PRODUCING NITROALKANES IN A MICROSTRUCTURED REACTOR

(71) Applicant: BASF SE, Ludwigshafen (DE)

(72) Inventors: Ralf Boehling, Lorsch (DE); Michael Hayer, Frankenthal (DE); Alwin Rehfinger, Mutterstadt (DE); Michael Schelper, Heidelberg (DE); Johann-Peter Melder, Boehl-Iggelheim (DE); Martin Ernst, Heidelberg (DE); Joaquim Henrique Teles, Waldsee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/768,391

(22) PCT Filed: Apr. 25, 2014

(86) PCT No.: PCT/EP2014/058437
§ 371 (c)(1),
(2) Date: Aug. 17, 2015

(87) PCT Pub. No.: WO2014/180678
PCT Pub. Date: Nov. 13, 2014

(65) Prior Publication Data
US 2015/0376111 A1 Dec. 31, 2015

(30) Foreign Application Priority Data
May 6, 2013 (EP) .................... 13166644

(51) Int. Cl.
C07C 205/00 (2006.01)
C07C 201/08 (2006.01)
B01J 19/00 (2006.01)

(52) U.S. Cl.
CPC .......... C07C 201/08 (2013.01); B01J 19/0093 (2013.01);
(Continued)

(58) Field of Classification Search
CPC .............................. C07C 21/06; C07C 205/02
USPC .......................................................... 568/947
See application file for complete search history.

(56) References Cited

U.S. PATENT DOCUMENTS

| 4,626,607 A | 12/1986 | Jacquinot et al. |
| 2010/0312003 A1 | 12/2010 | Brieden et al. |

FOREIGN PATENT DOCUMENTS

| EP | 0 174 600 A1 | 3/1986 |
| EP | 1 932 821 A1 | 6/2008 |
| EP | 2 048 129 A1 | 4/2009 |
| GB | 586 203 A | 3/1947 |
| WO | WO 2009/129099 A1 | 10/2009 |

OTHER PUBLICATIONS

Chemical Abstract, EP 1932821, Rehfinger et al, method for manufacturing oxidation products from cyclohexane using silicon coated micro channel reactor, Jun. 2008.*

(Continued)

*Primary Examiner* — Jafar Parsa

(74) *Attorney, Agent, or Firm* — Oblon, McClelland, Maier & Neustadt, L.L.P.

(57) ABSTRACT

The invention relates to a process for preparing nitroalkanes by reaction of at least one alkane with at least one nitrating agent in the gas phase, wherein the nitration is carried out in a microstructured reaction zone having parallel channels having hydraulic diameters of less than 2.5 mm and a total specific internal surface area of more than 1600 m²/m³ and the alkane and the nitrating agent are conveyed under a pressure of from 1 bar to 20 bar through the reaction zone and reacted at a temperature of from 150° C. to 650° C. and the reaction products are cooled downstream of the reaction zone and discharged and the at least one nitrating agent is introduced over from two to ten introduction points along the reaction zone.

15 Claims, 1 Drawing Sheet

(52) U.S. Cl.
CPC ............................ *B01J 2219/0086* (2013.01); *B01J2219/00792* (2013.01); *B01J 2219/00795* (2013.01); *B01J 2219/00824* (2013.01); *B01J 2219/00826* (2013.01); *B01J 2219/00831* (2013.01); *B01J 2219/00835* (2013.01); *B01J 2219/00842* (2013.01); *B01J 2219/00867* (2013.01); *B01J 2219/00873* (2013.01); *B01J 2219/00889* (2013.01); *B01J 2219/00891* (2013.01)

(56) References Cited

OTHER PUBLICATIONS

Chemical Abstract, Loewe et al, Multi-step processing in a microstructured flow reactor: direct nitration of propane—a proof of principle, Green processing and synthesis (2012), 1 (5), 439-448.*
International Search Report issued Jun. 11, 2014 in PCT/EP2014/058437.

* cited by examiner

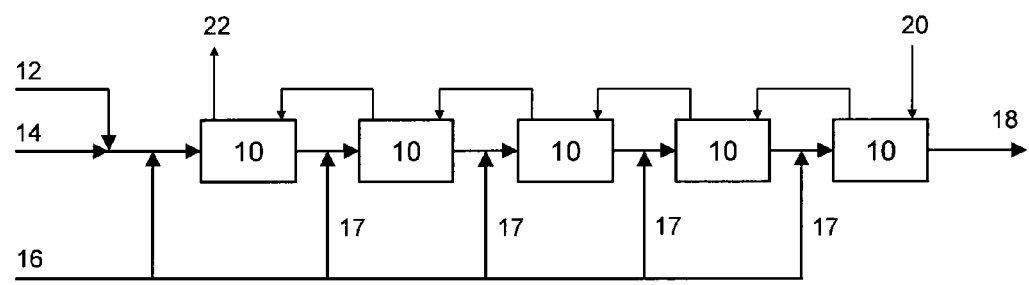

METHOD FOR PRODUCING NITROALKANES IN A MICROSTRUCTURED REACTOR

The invention relates to the preparation of nitroalkanes by reaction of at least one alkane with at least one nitrating agent in the gas phase.

Nitroalkanes are used as industrial solvents and are important synthetic building blocks for more complex molecules. The four most important nitroalkanes from an industrial point of view, namely nitromethane, nitroethane, 1-nitropropane and 2-nitropropane, are usually prepared by high-temperature vapor phase nitration of propane (Ullmann's Encyclopedia of Industrial Chemistry, "Nitro Compounds, Aliphatic", Chapter 3 "Production", Wiley-VCH Verlag, Weinheim, 2005). Nitric acid is used as nitrating agent for the reaction which proceeds by a free-radical mechanism, with the $NO_2$ radical representing the actual active species. The reaction is carried out at a temperature of from 350° C. to 450° C. and a pressure of from 8 to 12 bar. Control of the temperature in the strongly exothermic reaction is achieved in different ways, for example by means of a mode of operation using an excess of propane, spraying-in and vaporization of liquid nitric acid or shortening of the residence time in the reactor. The conversion of nitric acid into the target products is less than 50%. The predominant part reacts to form $NO_x$ and $N_2$, with the former being recovered. When excess propane is recirculated, from 60% to 80% of the propane can be converted into nitroalkanes.

The patent document U.S. Pat. No. 4,626,607 describes a process for preparing nitromethane. Here, methane is reacted with nitric acid or nitrogen dioxide in a homogeneous gas-phase reaction at pressures of from 1 to 35 bar and temperatures of from 270° C. to 600° C. in the presence of an activator. Activators used are halogens such as chlorine and bromine or derivatives thereof.

EP 0174600 B1 describes a process for preparing nitroalkanes and nitroaromatic compounds from an olefinically unsaturated hydrocarbon, for example an alkene such as propylene or butene. The olefin is brought into contact with nitrogen dioxide or nitric acid at a pressure of from 2 to 20 bar and a temperature of from 100° C. to 500° C. in a reaction zone.

Two-phase processes are also known. Thus, WO 2009/129099 A1 describes a production process for nitropropanes such as 2-nitropropane and 2,2-dinitropropane in a trickle-bed reactor. Here, gaseous propane flows in countercurrent to an aqueous nitric acid solution running virtually downward in the reactor at a pressure of from 68 to 109 bar and a temperature of from 215° C. to 325° C.

In all the known processes, a high outlay for safety is necessary because of the hazard potential of the substances used, and this requires complicated and expensive apparatuses. In addition, the selectivity to the desired nitroalkane is in most cases not satisfactory.

It is an object of the invention to provide a process which gives a high selectivity to the desired nitroalkanes. Here and in the following, selectivity is the ratio of the molar amount of nitroalkane formed to the molar amount of the alkane reacted. Furthermore, the process should be able to be carried out inexpensively in an apparatus which meets the demanding safety requirements necessary because of the participating materials.

This object is achieved by the subject matter of the invention as defined in claim 1. Further advantageous embodiments of the invention may be found in the dependent claims.

According to the invention, at least one alkane is reacted in the gas phase with at least one nitrating agent in a microstructured reaction zone. The at least one alkane can be present as pure material or as a mixture with other substances, for example as a mixture with other alkanes. The at least one alkane and the at least one nitrating agent are conveyed in gaseous form under a pressure of from 1 bar to 20 bar through the reaction zone and reacted at a temperature of from 150° C. to 650° C., preferably from 200° C. to 350° C., particularly preferably from 250° C. to 300° C. The reaction products are cooled downstream of the reaction zone and discharged for further use.

The pressure in the reaction zone is preferably set to as high as possible a value. However, it should be ensured that the starting materials and the reaction products are still present in vapor form in the reaction zone. In addition, it has to be ensured that in the case of detonation, the maximum detonation pressure occurring in the microstructured reaction zone can still be coped with.

The alkanes are preferably branched and/or unbranched alkanes having from one to twenty carbon atoms.

Suitable nitrating agents encompass nitric acid ($HNO_3$) and nitrogen oxides ($NO_x$), in particular nitrogen monoxide and nitrogen dioxide. Mixtures of nitrogen oxides and oxygen, in particular mixtures of nitrogen monoxide and oxygen, have been found to be particularly useful. In a preferred variant, nitrogen monoxide and oxygen are mixed to form nitrogen dioxide, before this nitrating agent mixture is brought into contact with the alkane.

For the purposes of the invention, a microstructured reaction zone is a zone of a reactor which is provided with parallel channels having hydraulic diameters of less than 2.5 mm, preferably less than 1.6 mm, and a specific internal surface area of more than 1600 $m^2/m^3$, preferably more than 2500 $m^2/m^3$. The hydraulic diameter ($d_h$) is generally defined as four times the ratio of flow cross section ($A_d$) and wetted circumference ($U_d$) of a tube or channel having a noncircular cross section, so that $d_h = 4 \cdot A_d/U_d$. The specific internal surface area ($A_{si}$) is equal to the ratio of wetting surface area ($A_b$) and volume (V) of the tube or channel, i.e. $A_{si} = A_b/V$. In the case of a rectangular channel cross section having a width b and a height h, for example, the hydraulic diameter is, under the assumption that the cross section does not change over the length of the channel, given by $d_h = 2 \cdot b \cdot h / (b+h)$ and, under the further assumption that the total internal surface area of the channel is wetted, the specific internal surface area is $A_{si} = 2 \cdot (b+h)/(b \cdot h)$. In the case of a circular channel cross section having the diameter "d", the hydraulic diameter is $d_h = d$ and the specific internal surface area is $A_{si} = 4/d$, under the same conditions.

The minimum dimension in any direction of a cross section through a channel is preferably 0.05 mm, particularly preferably 0.1 mm, in particular 0.2 mm. This value is determined by the manufacturing tolerance and the manufacturing outlay in the production of the microstructured reaction zone or the susceptibility to blockages. The channels in the reaction zone will hereinafter also be referred to as reaction channels. Such a reaction zone can be formed by components assembled in a modular fashion, with the individual components having holes or depressions at corresponding places so as to form, in the use configuration, channels through which the streams for the reaction or heat transport can be conveyed. Microstructured reactors display very good heat removal combined with very fast mass transfer. The wall thicknesses between the channels should be selected so that intrinsic safety in the case of potentially explosive mixtures is ensured.

In a preferred embodiment of the invention, the nitration is carried out in the presence of an inert or passivated internal surface of the microstructured reaction zone. To produce an inert or passivated internal surface, the reaction channels can be provided with a coating. Particular preference is given to the internal surface of the microstructured reaction zone being at least partly, in particular completely, provided with a silicon coating.

An inert or passivated internal surface of the reaction channels contributes to undesirable secondary reactions at the walls of the reaction channels being decreased or suppressed entirely, which has an advantageous effect on the selectivity and yield of the desired product.

In an alternative, preferred embodiment of the invention, the materials for producing the microstructured reaction zone are selected so that they have the same positive properties as the coating described above. Particular preference is given to the interior walls of the reaction channels being made of an inert material, in particular silicon, silicon carbide or a glass which in respect of inertness has comparable properties to those of fused silica or borosilicate glass. It is particularly advantageous for the entire microstructured reaction zone to be made of such an inert material.

A substantial advantage of the microstructured reaction zone compared to other reactor concepts is the possibility of making the reactor intrinsically safe. The wall thickness between two hollow spaces at any place in the microstructured reaction zone is particularly preferably selected so that intrinsic safety against detonative explosives is ensured.

The alkane or the mixture of alkanes is preferably mixed with the one or more nitrating agents so as to form a homogeneous gaseous reaction mixture before introduction into the reaction channels. If a starting material is present in liquid form, it is preferably firstly vaporized before being mixed with the other starting materials. Suitable microstructured mixing devices are known to those skilled in the art, as are suitable distributor structures in order to distribute the reaction mixture uniformly over the reaction channels. Mixing of the starting materials is advantageously carried out at below the reaction temperature at a pressure at which the participating materials are present in vapor form. This avoids an undesirable reaction of the mixture outside the reaction zone.

In a further preferred variant of the invention, at least part of the starting materials are mixed with one another only in the reaction zone. The introduction of the starting materials into the reaction zone can be effected in one stage, in a plurality of stages at a plurality of places or pseudocontinuously, for example via porous walls or membranes. In a particularly preferred embodiment, the at least one nitrating agent is introduced through from two to ten, in particular from four to six, feed points distributed along the reaction zone.

In an advantageous embodiment, in which a mixture of nitrogen oxides and oxygen is used as nitrating agent, it has been found to be advantageous to introduce a partial mixture which is rich in nitrogen oxide at the reactor inlet and to introduce an oxygen-rich partial mixture through the feed points along the reaction zone. It is particularly advantageous to introduce a partial mixture comprising predominantly oxygen through the feed points along the reaction zone; very particular preference is given to introducing elemental oxygen.

Nitrogen dioxide is in equilibrium with nitrogen monoxide and oxygen. Nitrogen dioxide decomposes into nitrogen monoxide and oxygen under the typical reaction conditions. It has been found to be advantageous to limit this dissociation of the nitrogen oxide to a maximum of 15%. The degree of dissociation can be influenced by selecting the pressure and temperature in the reaction zone adequately. Furthermore, intermediate introduction of an oxygen-rich partial mixture brings about a reduction in the degree of dissociation.

The molar ratio of alkanes to nitrating agent is preferably from 1:10 to 10:1, particularly preferably from 1:5 to 5:1. The reaction of alkanes with the nitrating agent(s) is preferably carried out at a residence time in the reaction channels of from 1 s to 600 s, in particular from 20 s to 200 s.

In a further embodiment, the nitration is carried out in the presence of a heterogeneous catalyst. The catalyst is preferably present in solid form, for example as a bed, in the reaction channels. The catalyst can also have been applied in the form of a coating to the internal walls of the reaction channels. In this case, the catalytic coating acts like an inert or passivated inner surface of the microstructured reaction zone in respect of undesirable secondary reactions.

In a further embodiment of the invention, one or more inert substances, preferably nitrogen or water, are additionally introduced into the reaction mixture. The inert substances are preferably introduced into the reaction mixture before entry into the reaction zone. In a further preferred variant, the inert substances are introduced into the reaction mixture within the reaction zone.

In an advantageous embodiment of the invention, these substreams from the reaction channels are combined after exit from the reaction zone and the reaction product is discharged. The gas and liquid phases formed on cooling of the reaction product can be separated from one another and subsequently be worked up by means of known methods such as fractional distillation. Unreacted starting materials can be recirculated to the microstructured reaction zone.

In a further advantageous embodiment of the invention, the reaction products are, after exit from the reaction zone, cooled by at least 10° C., preferably by at least 30° C., in a further microstructured zone. This zone will hereinafter also be referred to as quenching zone. The temperatures in the reaction zone and the quenching zone are preferably able to be regulated separately from one another. The rapid cooling of the reaction products after exit from the reaction zone reduces or completely prevents a possible further reaction outside the reaction zone, which has an advantageous effect on the desired selectivity.

In a further embodiment of the invention, the reaction products are fed to a further synthesis stage after exit from the reaction zone or the cooling zone. In this further synthesis stage, the nitroalkanes can, for example, be reacted with an aldehyde or ketone (Henry reaction) or in a Michael addition (e.g. nitriles or esters).

FIG. 1 schematically shows a preferred reactor concept for carrying out the process of the invention. The reactor concept provides a reactor cascade which is made up of a plurality of reactor modules 10 and in the examples shown has a five-stage configuration. Before entry into the first reactor module 10, the gaseous alkane via a first feedline 12 and the gaseous nitrating agent, preferably nitrogen monoxide, via a second feedline 14 are combined and mixed. Oxygen is subsequently introduced via an oxygen feedline 16 into the mixture and the resulting reaction mixture is fed into the first reactor module. Between the individual reactor modules 10, there is in each case an intermediate oxygen introduction 17, which can preferably be regulated individually in respect of the flow rate. To remove the heat involved in the reaction, a cooling medium flows through the reactor modules 10. In the example shown, the cooling medium flows in countercurrent to the reaction mixture through the reactor cascade. The cooling medium is fed via a cooling medium feed 20 into the reactor module farthest downstream in the cascade, flows through the modules of the series from the downstream end to the upstream end and leaves the farthest upstream module through a cooling medium outlet 22. Depending on the requirements for the heat to be removed, it is of course also possible to employ other cooling concepts, apart from the depicted series connection in countercurrent, for example also variants with cocurrent, cross-current or parallel flow. Corresponding arrangements and suitable cooling media are known to those skilled in the art.

Compared to the prior art, in which considerable excesses of alkane are necessary to achieve high space-time yields, a high selectivity of up to 63% of total nitroalkanes at conversions of up to 90% of total alkanes can be achieved by means of the process of the invention without excesses of alkanes. The microstructured reaction zone is not susceptible to malfunctions and can have a particularly small construction. Additional precautions for uniform distribution of the component mixture over the individual channels are not necessary. The synthesis can be carried out in an intrinsically safe manner in the microstructured reaction zone.

In a preferred embodiment of the process of the invention, propane is used to prepare 2-nitropropane highly selectively. Preferred nitrating agents in this case are nitric acid, nitrogen dioxide and a mixture of nitrogen monoxide and oxygen. In the reaction of propane with nitrogen dioxide or nitrogen monoxide, the ratio of the starting materials is preferably from 0.8 to 1.5 mol of $NO_x$/mol of propane.

In a further preferred embodiment of the process of the invention, isooctane is reacted with a mixture of nitrogen monoxide and oxygen to form nitroisooctane.

Compared to established methods of preparing nitroalkanes, the process of the invention has the advantages that, owing to the microstructured reaction zone, satisfactory and reliable temperature control and thus intrinsically safe operation is possible. The hazard potential is considerably reduced thereby. The apparatuses required have a simple construction, can be implemented inexpensively and can be scaled up or down in a modular fashion.

The process of the invention is illustrated by the following examples.

Nitration of Propane

The experimental setup for the synthesis of nitropropane corresponds essentially to the reactor concept depicted in FIG. 1, but the introduction of the starting materials is slightly modified. Nitrogen monoxide (NO) as nitrating agent and oxygen are introduced separately in gaseous form and related amounts into a first mixer from gas bottles, with nitrogen dioxide ($NO_2$) being formed straight away. The gas mixture is fed into a second mixer. Propane is firstly introduced in liquid form with a regulated flow from a steel bottle blanketed with He pressure through a thermostated zone set to 100° C. in a capillary. There, the propane vaporizes and is fed into the second mixer. From the second mixer, the reaction mixture is transferred into a first reactor module.

As reactor, a ⅛" capillary tube (internal diameter 1.4 mm) which is available in various lengths up to 60 m and is wound cylindrically was selected. It ensures satisfactory heat transfer and is located in a tubular hot air oven which can be regulated by means of fan heating to temperatures of up to 400° C. For this purpose, both the air temperature and the throughput of hot air are regulated appropriately. Outside the hot air oven, there is an additional protective heating facility in order to compensate for heat losses and thereby make it possible to ensure a uniform air temperature in the oven. The capillary tube is coated on its internal surface with silicon in order to make it inert. For comparative experiments, an uncoated capillary tube was used.

For the introduction of oxygen, a plurality of introduction points which are in the form of T-pieces are provided outside the oven housing. At these places, the reaction capillary is pulled out from the oven space, connected to the T-piece and pushed back into the furnace space. Here, the reaction capillary projects by not more than 5 cm from the furnace space. The oxygen is supplied in regulated amounts to the introduction points from a steel bottle.

The admission pressure into the mixer and into the reactor are limited by means of safety valves in the feedlines to the defined maximum pressure of the synthesis, in this case 15 bar.

The product mixture leaving the capillary reactor is introduced into a zone which is maintained at about 200° C. in order to prevent condensation. The gas mixture is depressurized under pressure regulation to ambient pressure and fed via a sampling valve to a gas chromatograph for on-line analysis. From there, the gas stream goes into a quenching vessel in which the gas stream is passed into a quenching liquid where it at least partly condenses out. As quenching liquid, use is made of, for example, a 40% strength aqueous isopropanol solution or n-butanol.

EXAMPLE 1

The length of the capillary reactor was 60 m, and the reactor volume was 92 ml. As starting materials, 5 standard l/h of propane and also nitrogen monoxide and oxygen were fed to the reactor in a molar ratio of propane:NO:$O_2$=1:1:0.5. The reactor was maintained at a pressure of 12 bar and the temperature was kept at 250° C. Analysis of the product mixture indicated a selectivity of propane to 2-nitroproane of 54% at a propane conversion of 49%.

EXAMPLE 2

The reactor configuration and the operating conditions corresponded to those in example 1. However, oxygen was introduced in a superstoichiometric amount. The molar ratio of the starting materials was propane:NO:$O_2$=1:1:1. Analysis of the product mixture indicated a selectivity of propane to 2-nitropropane of 42% at a propane conversion of 78%.

EXAMPLE 3

Intermediate Introduction of $O_2$

In further experiments, the molar ratio of the starting materials was again changed to propane:NO:$O_2$=1:1.2:1.2, with the oxygen being introduced in equal parts (3×0.4) at the reactor inlet, at a first introduction point at 20 m along the reactor and at a second introduction point at 40 m along the reactor. This mode of operation with intermediate introduction of oxygen was tested for different temperatures and different amounts of starting materials. The pressure in the reactor was in each case 12 bar. The results are shown in the following table. The selectivity of propane to other nitroalkanes (1-nitropropane, nitroethane and nitromethane) was in total in the range from 9% to 13% for the experimental results shown.

| Propane feed rates [standard l/h] | Temperature [° C.] | Selectivity to 2-nitropropane [%] | Propane conversion [%] |
|---|---|---|---|
| 5 | 250 | 51 | 85 |
| 5 | 270 | 52 | 89 |
| 10 | 250 | 48 | 74 |
| 10 | 270 | 49 | 82 |
| 10 | 290 | 49 | 84 |
| 20 | 270 | 47 | 74 |
| 20 | 290 | 47 | 82 |

In a smaller reactor, the experiments described below were carried out using nitric acid ($HNO_3$) and nitrogen dioxide ($NO_2$) as starting materials:

EXAMPLE 4

For the nitration of propane using concentrated nitric acid (65%), a stream of 5.6 standard l/h of propane and a stream of 6.2 g/h of $HNO_3$ (65%) were each fed continuously as starting materials into a 1/16" stainless steel capillary having a circular cross section and an internal diameter of 0.76 mm and a length of in each case 3 m at a pressure of 2 bar in a molar ratio of propane to $HNO_3$ of 4:1. The capillaries were located in an oven space which was maintained at a temperature of 210° C. by means of hot air. The starting materials vaporized in the capillaries and were, still in the oven space, mixed with one another at 250° C. via a T-piece in a second zone and subsequently introduced into an arrangement having four parallel reaction capillaries which were located in a second oven space following the first oven space. The reaction capillaries were maintained at a temperature of 320° C. by means of hot air. Each of the four parallel reaction capillaries was a 1/16" stainless steel capillary which had a circular cross section, an internal diameter of 0.76 mm and a length of 10 m and was coated on the inside with silicon. The total reaction volume of the four parallel channels was 18.2 ml. The distribution of the streams over the four capillaries and the subsequent recombination thereof was effected by means of in each case three T-pieces in such a way that equal flow paths were obtained in order to ensure uniform flow through the four channels. The pressure in the reaction capillaries was maintained at 2 bar. The residence time of the reaction mixture in the reaction capillaries was about 4 s. Analysis of the product mixture indicated (figures in % by area) 97.6% of propane, 1.0% of 2-nitropropane and 0.6% of 1-nitropropane. Under otherwise identical experimental conditions, the following results were obtained for higher temperatures in the reaction capillaries:
93.3% of propane, 2.5% of 2-nitropropane and 1.7% of 1-nitropropane at 340° C.,
91.1% of propane, 3.3% of 2-nitropropane and 2.6% of 1-nitropropane at 360° C.,
89.8% of propane, 3.2% of 2-nitropropane and 3.2% of 1-nitropropane at 380° C.

EXAMPLE 5

A stream of 9.1 g/h of propane and a stream of 9.7 g/h of $NO_2$ were each continuously fed separately as starting materials into a 1/16" stainless steel capillary having a circular cross section and an internal diameter of 0.76 mm and a length of in each case 3 m at a pressure of 12 bar. The capillaries were located in an oven space which was maintained at a temperature of 280° C. by means of circulating air. The starting materials vaporized in the capillaries and were mixed with one another by means of a T-piece at 250° C. in a second zone following the oven space and subsequently introduced into a reaction capillary which was located in the same oven space at a temperature of 280° C. The reaction capillary was a 1/16" capillary which had a circular cross section and an internal diameter of 0.76 mm, a length of 7 m and a volume of 3.5 ml and was coated on the inside with silicon. The residence time of the reaction mixture in the reaction capillary was 8 s. The end of the reaction zone was located outside the oven space in a region maintained at 250° C. The product mixture was immediately mixed there with a stream of 2.5 g/h of steam, depressurized via a pressure regulating valve to 1 bar and cooled to 20° C. in a double-walled tube. Both the gas phase and the two-phase liquid output were analyzed. The propane conversion was 6% at a selectivity of propane to nitroalkanes of 84%. The selectivities to the individual components were 69%, 12%, 1% and 2% for 2-nitropropane, 1-nitropropane, nitroethane and nitromethane. As by-products, 7% of methanol, 8% of acetone and 1% of acetic acid were found.

EXAMPLE 6

In the same experimental setup as described in example 1, a stream of 54 g/h of propane and a stream of 10 g/h of $NO_2$ were separately fed in continuously as starting materials. The pressure in the capillaries was 12 bar, and the oven space was maintained at 400° C. The zone outside the oven space had a temperature of 250° C. The residence time in the reaction capillaries was 1.9 s. At the outlet from the reaction capillaries, the product mixture was mixed with a stream of 2.5 g/h of steam, depressurized via a pressure regulating valve to 1 bar and cooled to 20° C. in a double-walled tube. The two-phase liquid output was analyzed. Based on the organic products formed and present in the liquid phase, which amounted to 0.12 g/h, 7% of acetic acid, 28% of nitropropanes, 4% of nitroethane and 12% of nitromethane were found.

COMPARATIVE EXAMPLE FOR EXAMPLE 6

For comparison, example 6 was modified by using a reaction capillary which was not coated with silicon. The starting material streams were 51 g/h of propane and 11 g/h of $NO_2$, and the stream of steam added to the product mixture amounted to 5.6 g/h. Pressure and temperatures were identical to those in example 6. The residence time in the reaction capillaries was 2.0 s. Based on the organic products formed and present in the liquid phase, which amounted to 0.1 g/h, 20% of acetic acid, 7% of nitropropanes, 2% of nitroethane and 14% of nitromethane were found by analysis.
Nitration of Isooctane The experimental setup for the synthesis of nitroisooctane corresponded essentially to the reactor concept shown in FIG. 1. However, the maximum system pressure was limited to 5 bar and the originally liquid starting material isooctane was vaporized at 200° C. in a capillary.

EXAMPLE 7

A stream of 1 standard l/h of NO and a stream of 1 standard l/h of $O_2$ were fed separately in gaseous form and regulated amounts into a first mixer from gas bottles, with nitrogen oxide ($NO_2$) being formed. This gas mixture fed as nitrating agent into a second mixer. Both mixers were present in a thermostat set to 200° C. A stream of 2 standard l/h corresponding to 10.2 g/h, of isooctane was fed into a 1/16" capillary present in the same thermostated zone. The isooctane vaporized and was fed to the second mixer where it mixed with the nitrating agent. From the second mixer, the reaction mixer was transferred into the reactor which was configured as a 1/8" capillary tube having an internal diameter of 1.4 mm. The internal surface of the tube was coated with silicon, and its length was 15 m. The capillary tube was wound up cylindrically and was located in a tubular hot air oven which was maintained at 250° C. by fan heating. The pressure in the feedlines, the thermostated zone and the reactor was 5 bar.

The product stream leaving the reactor was maintained at about 200° C. in order to prevent condensation of product, depressurized under pressure regulation to ambient pressure and passed via a sampling valve to analysis. From the on-line analysis, the gas stream was conveyed further into a quenching vessel in which the liquid reaction products were diluted under atmospheric pressure in n-butanol as quenching liquid. In the on-line gas analysis, 69% by area of isooctane and 8.3% by area of nitroisooctane were found. The conversion of isooctane was 33%, and the selectivity to nitroisooctane was 25%.

EXAMPLE 8

The experimental setup as per example 7 was varied by using a 60 m long 1/8" capillary tube as reactor. Furthermore, two feedlines for the intermediate introduction of oxygen were provided; these were located one third and two thirds along the length of the reactor. The isooctane stream was 8 standard l/h, corresponding to 40.8 g/h, and the NO stream was 4 standard l/h. This was mixed with a stream of 1.33 standard l/h of 02, and 1.33 standard l/h of $O_2$ were introduced via each of the intermediate introduction points into the reaction mixture, i.e. a total of likewise 4 standard l/h of oxygen. In the on-line analysis, 14.2% by area of isooctane and 25.3% by area of nitroisooctane were found. The conversion of isooctane was increased to 88% at a selectivity to nitroisooctane of 29%.

The invention claimed is:

1. A process comprising preparing nitroalkanes by reaction of at least one alkane with at least one nitrating agent in the gas phase, wherein the nitration is carried out in a microstructured reaction zone having parallel channels having hydraulic diameters of less than 2.5 mm and a total specific internal surface area of more than 1600 $m^2/m^3$, where the alkane and the nitrating agent are conveyed under a pressure of from 1 bar to 20 bar through the reaction zone and reacted at a temperature of from 150° C. to 650° C. and the reaction products are cooled downstream of the reaction zone and discharged and the at least one nitrating agent is introduced over from two to ten introduction points along the reaction zone, wherein the at least one nitrating agent which is introduced via the from two to ten introduction points comprises an oxygen-rich partial mixture comprising a mixture of oxygen and at least one nitrogen oxide.

2. The process according to claim 1, wherein the nitration is carried out in the presence of an inert or passivated internal surface of the microstructured reaction zone.

3. The process according to claim 2, wherein the internal surface of the microstructured reaction zone is provided with a silicon coating.

4. The process according to claim 2, wherein the interior walls of the reaction channels are made of an inert material.

5. The process according to claim 1, wherein the wall thickness between two hollow spaces at every place in the microstructured reaction zone is selected so that intrinsic safety in respect of detonative explosions is ensured.

6. The process according to claim 1, wherein inert substances are additionally added to the reaction mixture.

7. The process according to claim 1, wherein the reaction products are cooled by at least 10° C. in a further microstructured zone after exit from the reaction zone.

8. The process according to claim 1 comprising preparing nitropropanes by reaction of propane with a nitrating agent at a pressure of from 1 bar to 20 bar and a temperature of from 200° C. to 350° C.

9. The process according to claim 1 comprising preparing nitroisooctane by reaction of isooctane with a nitrating agent at a pressure of from 1 bar to 20 bar and a temperature of from 200° C. to 350° C.

10. The process according to claim 4, wherein the inert material is silicon, silicon carbide or a glass which in respect of inertness has comparable properties to fused silica or borosilicate glass.

11. The process according to claim 1, wherein the oxygen-rich partial mixture is a partial mixture comprising predominantly oxygen.

12. The process according to claim 6, wherein the inert substances are nitrogen or water.

13. The process according to claim 7, wherein the reaction products are cooled by at least 30° C.

14. The process according to claim 8, wherein the nitrating agent further comprises nitric acid.

15. The process according to claim 9, wherein the nitrating agent further comprises nitric acid.

* * * * *